US011471178B2

(12) United States Patent
Brasset et al.

(10) Patent No.: US 11,471,178 B2
(45) Date of Patent: Oct. 18, 2022

(54) INSTRUMENT FOR SELECTIVELY GRABBING AND CUTTING TISSUE

(71) Applicant: Asensus Surgical US, Inc., Durham, NC (US)

(72) Inventors: Damien Brasset, Milan (IT); Stefano Maghini, Vimodrone (IT); Riccardo Pozzato, Voghera (IT)

(73) Assignee: Asensus Surgical US, Inc., Durham, NC (US)

( * ) Notice: Subject to any disclaimer, the term of this patent is extended or adjusted under 35 U.S.C. 154(b) by 13 days.

(21) Appl. No.: 16/931,440

(22) Filed: Jul. 16, 2020

(65) Prior Publication Data

US 2021/0038241 A1 Feb. 11, 2021

Related U.S. Application Data

(60) Provisional application No. 62/874,980, filed on Jul. 16, 2019.

(51) Int. Cl.
*A61B 17/285* (2006.01)
*A61B 34/30* (2016.01)
*A61B 17/28* (2006.01)

(52) U.S. Cl.
CPC .......... *A61B 17/285* (2013.01); *A61B 17/282* (2013.01); *A61B 17/2816* (2013.01); *A61B 34/30* (2016.02)

(58) Field of Classification Search
CPC . A61B 17/282; A61B 17/285; A61B 17/2816; A61B 17/2938; A61B 17/295; A61B 17/2906; A61B 17/2929; A61B 2017/00353; A61B 34/30
USPC ......................................... 606/205, 210, 211
See application file for complete search history.

(56) References Cited

U.S. PATENT DOCUMENTS

| 8,920,460 B2 * | 12/2014 | Schweitzer | ............ | A61B 17/29 |
| | | | | 606/205 |
| 2020/0022765 A1 * | 1/2020 | Limon | ................... | A61B 34/74 |

* cited by examiner

*Primary Examiner* — Elizabeth Houston
*Assistant Examiner* — Serenity A Miller

(57) ABSTRACT

A surgical instrument configured for both grasping and cutting operations has a shaft with a push rod extending through it. An end effector on the shaft has a grasping jaw, a cutting jaw, and an intermediate jaw. The grasping jaw forms a grasping device with the intermediate jaw, and the cutting jaw forming a cutting device with the intermediate member. A segment of the shaft proximal to the end effector is axially rotatable between a first position, in which the push rod can advance through the segment to actuate the cutting device, and a second position in which the push rod can advance through the segment to actuate the grasping device.

7 Claims, 3 Drawing Sheets

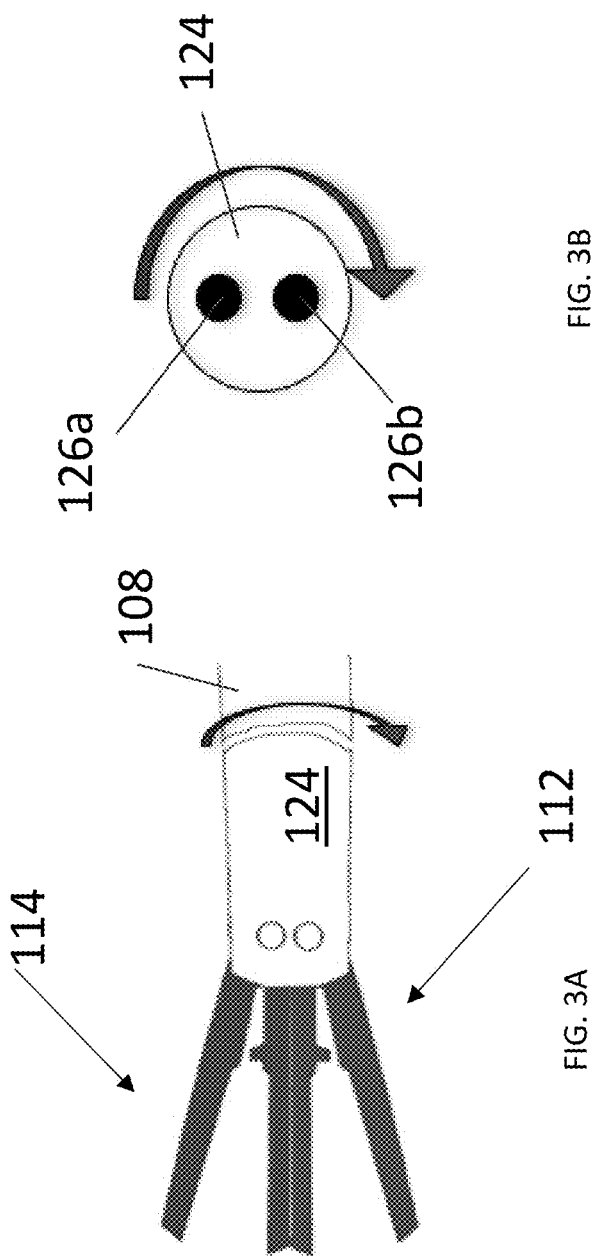

INSTRUMENT FOR SELECTIVELY GRABBING AND CUTTING TISSUE

This application claims the benefit of U.S. Provisional Application No. 62/874,980. Inventors: Damien Brasset, Stefano Magnini, Riccardo Pozzato.

BACKGROUND

Surgical robotic systems are typically comprised of one or more robotic manipulators and a user interface. The robotic manipulators carry surgical instruments or devices used for the surgical procedure. A typical user interface includes input devices, or handles, manually moveable by the surgeon to control movement of the surgical instruments carried by the robotic manipulators. The surgeon uses the interface to provide inputs into the system and the system processes that information to develop output commands for the robotic manipulator.

In the system illustrated in FIG. 1, a surgeon console 12 has two input devices or handles 17, 18. The input devices are configured to be manipulated by a user to generate signals that are used to command motion of a robotically controlled device in multiple degrees of freedom. In use, the user selectively assigns the two input devices to two of the robotic manipulators 13, 14, 15, allowing surgeon control of two of the surgical instruments 10a, 10b, and 10c disposed at the working site at any given time. To control a third one of the instruments disposed at the working site, one of the two input devices is operatively disengaged from one of the initial two instruments and then operatively paired with the third instrument. A fourth robotic manipulator, not shown in FIG. 1, may be optionally provided to support and maneuver an additional instrument.

One of the instruments 10a, 10b, 10c is a camera that captures images of the operative field in the body cavity. The camera may be moved by its corresponding robotic manipulator using input from a variety of types of input devices, including, without limitation, one of the new haptic interface devices, the handles 17, 18, additional controls on the console, a foot pedal, an eye tracker 21, voice controller, etc. The console may also include a display or monitor 23 configured to display the images captured by the camera, and for optionally displaying system information, patient information, etc.

A control unit 30 is operationally connected to the robotic arms and to the user interface. The control unit receives user input from the input devices corresponding to the desired movement of the surgical instruments, and the robotic arms are caused to manipulate the surgical instruments accordingly.

The input devices are configured to be manipulated by a user to generate signals that are processed by the system to generate instructions used to command motion of the manipulators in order to move the instruments in multiple degrees of freedom.

The surgical system allows the operating room staff to remove and replace surgical instruments carried by the robotic manipulator, based on the surgical need. Once instruments have been installed on the manipulators, the surgeon moves the input devices to provide inputs into the system, and the system processes that information to develop output commands for the robotic manipulator in order to move the instruments and, as appropriate, operate the instrument end effectors. While necessary, instruments take time during the course of a surgical procedure. The instrument described in this application helps to eliminate delays resulting from instrument exchanges by including multiple functions in one surgical instrument.

BRIEF DESCRIPTION OF THE DRAWINGS

FIG. 3A is similar to FIG. 2 and illustrates rotation of the shaft tip relative to the shaft during instrument selection.

FIG. 3B is a cross-section view of the shaft tip.

DETAILED DESCRIPTION

Figure 1:
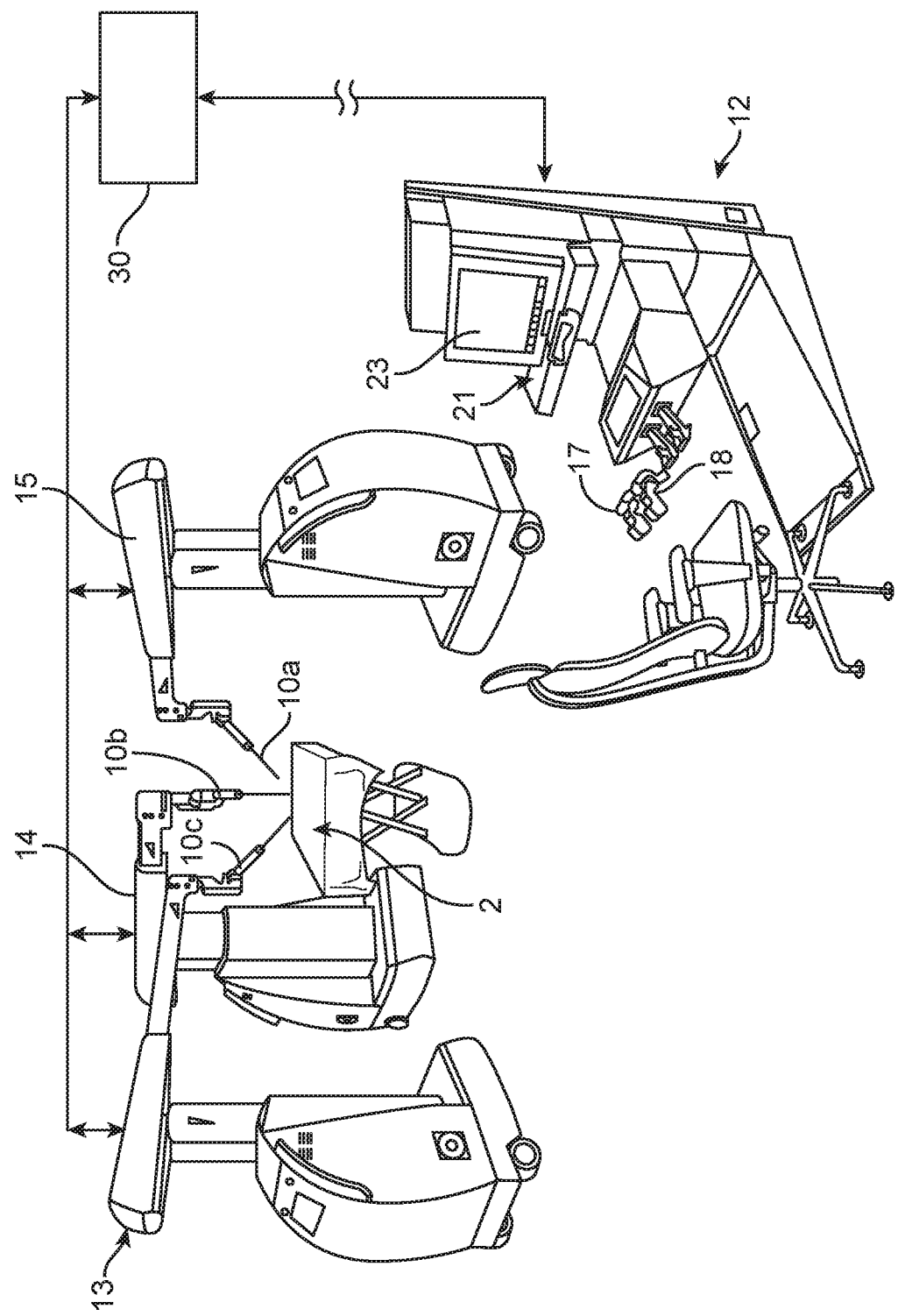
FIG. 1 shows an example of a robot-assisted surgical system.
Figure 2:
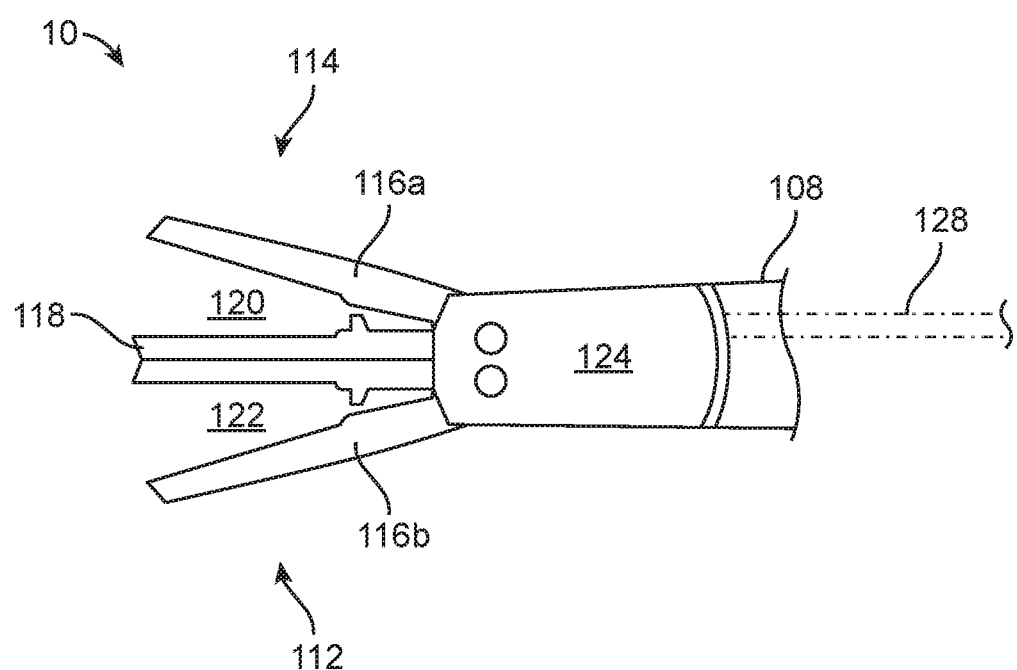
FIG. 2 shows an end effector of an embodiment of a surgical instrument employing separate grab and cut features.

Referring to FIG. 2, a surgical instrument 10 includes an end effector having a grasping part 112 and a cutting part 114. The end effector is disposed on a shaft 108.

In the illustrated embodiment, the end effector is formed by a pair of pivoting jaw members 116a, 116b and a central member 118. The jaw member 116a and the central member 118 form the cutting part 112, which includes at least one cutting surface facing into a cutting jaw opening 120. The jaw member 116b and the central member 118 form the grasping part having a grasping jaw opening 122 and grasping surfaces on the jaw member 116b and the portion of the central member on the grasping side, facing the grasping jaw opening 122. The jaw openings 120, 122 are separate openings in this embodiment.

In alternative embodiments, the central member 18 may be two separate members, one used for the grasping part and one used for the cutting part.

A shaft tip 124 of the end effector is rotatable on the shaft 108. As shown in the cross-section view of the shaft tip that is shown in FIG. 3B, the shaft tip 124 includes a pair of longitudinal through-holes in parallel to one another. Within the shaft 108 is a push rod 128 that is moveable longitudinally in proximal and distal directions. Depending on the rotational orientation of the distal part 214, the push rod aligns and enters either the through-hole 126a corresponding to the cutting part, or through-hole 126b corresponding to the grasping part. Actuation of the push rod to move includes use of electromechanical actuators in the manipulator or carried by the instrument to cause operation of the corresponding part 112, 114.

To change the tip selection from one part to the other, the user enters input at the user input device of the surgical system, which causes electromechanical actuators in the manipulator or the instrument to effect rotation of the shaft tip 124 relative to the shaft 108.

The actuation mechanism of the instrument is preferably configured so that distal movement of the push rod 128 causes opening of the corresponding jaws (which, as discussed above, depends on whether the cutting part or the grasping part is aligned with the push rod). Whichever of the cutting part and distal part is not positioned to be actuated will remain in the closed position during actuation of the other part. Note that FIGS. 2 and 3 show both the cutting part and grasping part in open positions for purposes of simplicity, since at any given time both the grasping and cutting parts will be closed, or one will be open and the other closed.

We claim:

1. A surgical instrument comprising:
    an elongate shaft having a push rod longitudinally extending therethrough;

a shaft tip on the shaft, the shaft tip including first and second through-holes, the shaft tip axially rotatable relative to the shaft between a first position in which the push rod is longitudinally aligned with the first through-hole, and a second position in which the push rod is longitudinally aligned with the second through-hole;

an end effector including a grasping jaw, a cutting jaw, and at least one intermediate jaw, said grasping jaw forming a grasping device defining a grasping jaw opening with at least one of said at least one intermediate jaw, and said cutting jaw forming a cutting device having a cutting jaw opening with at least one of said at least one intermediate jaw;

wherein when the shaft tip is in the first position, the push rod is longitudinally advanceable into the shaft tip to close the grasping jaw, and wherein when the shaft tip is in the second position, the push rod is longitudinally advanceable into the shaft to close the cutting jaw.

2. The surgical instrument of claim 1, wherein the grasping jaw opening and cutting jaw opening are separate openings.

3. The surgical instrument of claim 1, wherein the grasping device has a closed position and wherein the grasping device is configured to remain in the closed position when the shaft tip is in the second position.

4. The surgical instrument of claim 1, wherein the cutting device has a closed position and wherein the cutting device is configured to remain in the closed position when the shaft tip is in the first position.

5. The surgical instrument of claim 1, wherein each of the cutting device and the grasping device has a closed position, and wherein each of the cutting device and the grasping device is in its corresponding closed position when the push rod occupies neither the first nor the second through-hole.

6. A surgical robotic system including a robotic manipulator, the instrument of claim 1 on the robotic manipulator, and a user input device, at least one processor, and at least one memory storing instructions executable by said at least one processor to receive tip selection input from the user input device, and, in response to the tip selection input, axially positioning the shaft tip to position the first or second through-hole in alignment with the push rod.

7. The surgical robotic system of claim 6, wherein the instructions are further executable by said at least one processor to actuate the pushrod to close the grasping jaws or the cutting jaws.

* * * * *